US00PP23933P3

(12) United States Plant Patent
Shefelbine

(10) Patent No.: US PP23,933 P3
(45) Date of Patent: Oct. 1, 2013

(54) APPLE TREE 'DS 22'

(50) Latin Name: *Malus domestica*
Varietal Denomination: DS 22

(76) Inventor: Doug Shefelbine, Holman, WI (US)

( * ) Notice: Subject to any disclaimer, the term of this patent is extended or adjusted under 35 U.S.C. 154(b) by 408 days.

(21) Appl. No.: 13/065,210

(22) Filed: Mar. 15, 2011

(65) Prior Publication Data

US 2012/0240296 P1 Sep. 20, 2012

(51) Int. Cl.
*A01H 5/00* (2006.01)

(52) U.S. Cl.
USPC ..... Plt./161

(58) Field of Classification Search
USPC ..... Plt./161
See application file for complete search history.

(56) References Cited

PUBLICATIONS

Lehnert, Richard "DS 22 planned for this fall." Good Fruit Grower, Jun. 2012.*

* cited by examiner

*Primary Examiner* — Wendy C Haas
(74) *Attorney, Agent, or Firm* — Paine Hamblen, LLP

(57) ABSTRACT

A new and distinct variety of apple tree is described and which is somewhat similar in its overall characteristics to that of the 'Honeycrisp' apple tree (U.S. Plant Pat. No. 7,197), but which is distinguishable therefrom by producing a fruit which is ripe for harvesting and shipment about 5 days earlier than the 'Honeycrisp' apple tree when grown under the prevailing ecological conditions which occur near Ephrata, Wash.

3 Drawing Sheets

Latin name: *Malus domestica.*
Varietal denomination: DS 22.

BACKGROUND OF THE NEW VARIETY

The present invention relates to a new, novel, and distinct variety of apple tree, *Malus domestica,* and which has been denominated varietally as 'DS 22', and more specifically, to a novel apple tree which produces fruit which are ripe for harvesting and shipment at least about five days earlier than the variety it's most closely similar to, that being the 'Honeycrisp' apple tree (U.S. Plant Pat. No. 7,197) when it is grown under the same cultural conditions, and at the same geographical location.

ORIGIN AND ASEXUAL REPRODUCTION

It has long been recognized that an important factor contributing to the success of any new variety of apple tree, that is *Malus domestica*, bearing fresh market fruit, is its relative date of harvesting in comparison to other varieties bearing similar fruit in the same season. Further, another significant factor affecting the commercial viability of any new variety of apple relates to its fruit appearance, as well as its storage traits, and which are reflected by such pomological characteristics as the starch level and fruit pressure of same.

The new variety of apple tree, as described herein, 'DS 22', was derived by the following methodology. Seeds from an open pollinated 'Honeycrisp' apple tree (U.S. Plant Pat. No. 7,197) were collected during the 1990 growing season. These same seeds were then planted in 1991 at an orchard nursery, which is located near Holman, Wis. This orchard is located in USDA hardiness zone 4A. The seeds which were planted in 1990 were cared for, and observed, and the new variety DS 22 was selected from among surviving seedlings during the 2002 growing season. Bud wood was later removed from this promising seedling and was then grafted into M26 rootstock (unpatened). This rootstock was then planted in a test nursery which is located near Ephrata, Wash., in 2008. The test orchard in Ephrata, Wash. is located in USDA Hardiness Zone 6A. Subsequently, these test trees have been observed, and it has been determined that the fruit produced from same, and the tree characteristics thereof, are the same as that seen in the original seedling that was first identified in 2002.

SUMMARY OF THE PRESENT VARIETY

The 'DS 22' apple tree is characterized as to novelty by producing an attractively colored fruit which is ripe for harvesting and shipment about September $4^{th}$ under the ecological conditions prevailing in Ephrata, Wash. This date of harvesting is about five (5) days earlier than the closest known variety, that being, the 'Honeycrisp' apple tree (U.S. Plant Pat. No. 7,197) from which it was derived as a chance seedling. The new variety produces apples which are characterized by having a blotchy striped skin which covers over about two-thirds of the fruit surface, as compared to the lightly striped blush that covers 80% to 90% of the fruit produced by the 'Honeycrisp' apple tree (U.S. Plant Pat. No. 7,197). Still further, the present variety produces fruit having a sugar content that is less than that of the 'Honeycrisp' apple tree, and further has less fruit pressure as compared to the fruit produced by the 'Honeycrisp' apple tree. Finally, the present variety 'DS 22' also produces fruit which resists browning after it is exposed to ambient air.

BRIEF DESCRIPTION OF THE DRAWINGS

The accompanying drawings are color photographs of the present variety.

Figure 1:
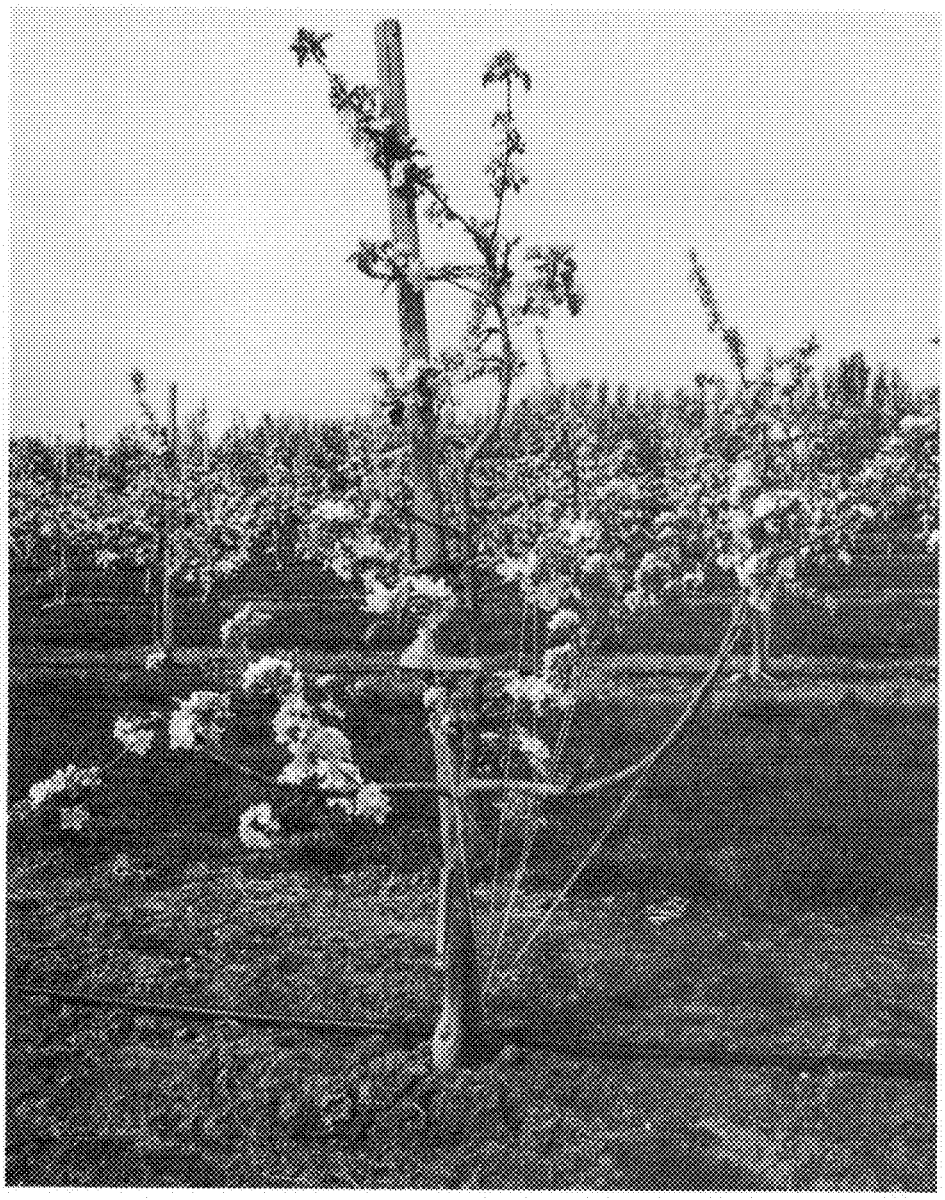
FIG. 1 depicts a second generation tree of the present variety at full bloom.
Figure 2:
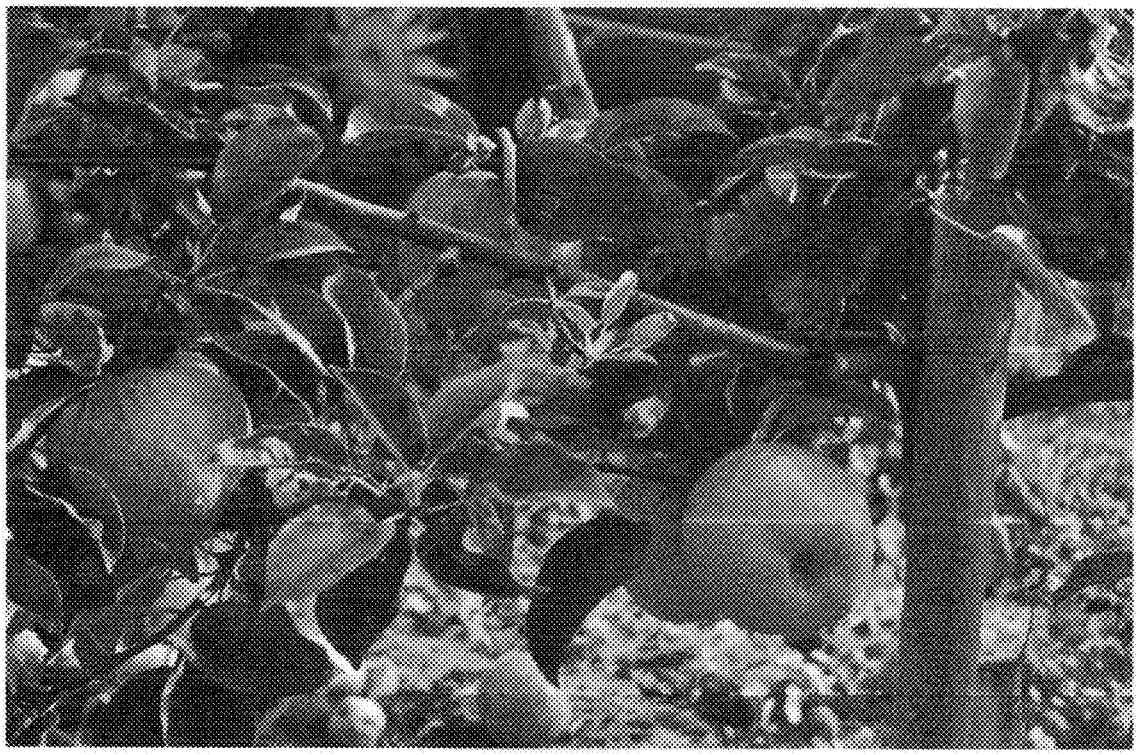
FIG. 2 depicts the fruiting characteristic of a second generation tree of the present variety at full harvest maturity.
Figure 3:
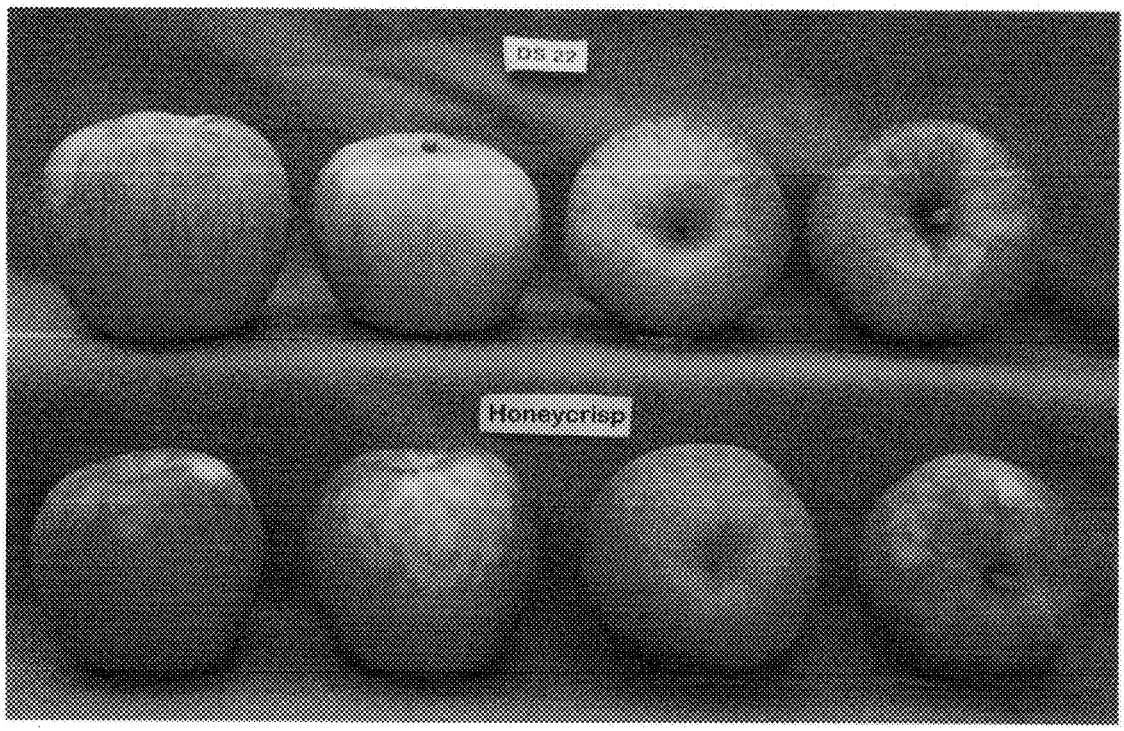
FIG. 3 shows the fruit of the present variety 'DS 22' as compared to the fruit of the 'Honeycrisp' apple tree (U.S. Plant Pat. No. 7,197) at full harvest maturity.

The colors in the enclosed photographs are as nearly true as is reasonably possible in color photographs of this type. However, due to chemical development, processing and printing, the leaves and fruit depicted in these photographs may or may not be accurate when compared to the actual botanical specimens. For this reason, future color references should be made to the color plates (Royal Horticulture Society of Great Britain) and the other common color have descriptions, as provided hereinafter.

NOT A COMMERCIAL WARRANTY

The following detailed description has been prepared to solely comply with the provisions of 35 U.S.C. §112, and does not constitute a commercial warranty (either expressed or implied) that the present variety will, in the future, display the botanical, pomological, or other characteristics as set forth, hereinafter. Therefore, this disclosure may not be relied upon to support any future legal claims including, but not limited to, breach of warranty of merchantability, or fitness for any particular purpose, which is directed, in whole or in part to the present variety.

DETAILED DESCRIPTION

Referring more specifically to the pomological and botanical details of this new and distinct variety of apple tree, the following has been observed during the 2010 growing season under the ecological conditions then prevailing in a test orchard which is located near Ephrata, Wash. All major color code designations are by reference to The R.H.S. Colour Chart (Third Edition) provided by The Royal Horticultural Society of Great Britain.

TREE

*Size.*—Generally considered average for the species.

*Tree height.*—About 7 feet.

*Crown width.*—About 5 feet. The tree is considered to have moderately heavy spur development, and is otherwise considered precocious. Currently the observed trees are growing in an orchard having a central leader type arrangement.

*Vigor.*—Considered moderate for the species.

*Hardiness.*—Considered hardy in USDA Zone 4b.

*Trunk size.*—About 4.1 cm in diameter when measured at a height of about 20 cm above the graft union.

*Bark texture.*—Glabrous.

*Bark color.*—Gray/brown (RHS Group 199A).

*Lenticels.*—Generally — Present and moderate in number. Typically about 13 lenticels are found per a four square cm area of the trunk.

*Lenticels.*—Shape — Elongated, and having an average width of about 1 mm; and an average length of about 6 mm.

*Lenticels.*—Color — Orange/white (RHS Group 159D).

*First year branches.*—Diameter — When measured at the mid-point of growth, the diameter of the branches is about 4.5 to about 6.7 mm.

*First year branch color.*—Gray/orange (RHS Group N199C).

*First year branch lenticels.*—Numbers — Numerous, typically about 13 lenticels are found per square centimeter of branch surface area.

*Lenticels.*—Shape — Oval.

*Lenticels.*—Length — About 0.9 mm.

*Lenticels.*—Width — About 0.5 mm.

*Lenticels.*—Color — White (RHS Group 155D).

*First year branch pubescence.*—Present and moderate in abundance.

*First year branch pubescence.*—Color — White. This color is not distinctive of the variety.

*Internodes.*—Size — About 3.1 cm to about 4.1 cm in width.

*Dormant fruiting buds.*—Shape — Considered generally beehive in shape and conical.

*Fruiting buds.*—Length — about 4.1 mm.

*Fruiting buds.*—Basal Diameter — about 6.4 mm.

*Two year old branches.*—Generally — These are not distinctive of the present variety.

*Diameter.*—When measured at the mid-point of growth, the diameter is about 6.5 to 7.7 mm.

*Spur development.*—Generally — considered moderate.

*Spur length.*—About 1 cm to about 3 cm.

*Lenticel numbers.*—Numerous lenticels are present. On average, about 10 lenticels are found per square centimeter of surface area.

*Lenticels.*—Shape — About 1-2 mm in diameter, and generally round, although occasionally elongated ones are found which have a length of about 1.5 mm.

*Scaffold branches.*—Size — Scaffold branches have a diameter of about 3.3 cm to about 4.6 cm when measured at a distance of about 10 cm from the trunk.

*Crotch angle.*—This is not distinctive of the present variety. However, as the tree is currently trained, the crotch angle is moderate, to flat, that is, ranging from about 60 to about 90 degrees from the vertical.

*Scaffold branches.*—Color — Gray/brown (RHS N199A).

*Scaffold branches.*—Lenticels — Generally these are numerous in number and average about 8 per square centimeter of surface area.

*Scaffold branch lenticels.*—Shape — Elongated and small. These lenticels have a length of about 4.8 mm and a width of about 1 mm.

*Scaffold branch lenticels.*—Color — Gray/yellow (RHS Group 161D).

LEAVES

*Shape.*—Considered broadly acute and generally upwardly folded.

*Surface texture.*—Dorsal Surface — Leathery and slightly undulating.

*Surface texture.*—Ventral Surface — Glabrous.

*Leaf sheen.*—Dorsal Surface — The variety has a high sheen.

*Leaf sheen.*—Ventral Surface — The appearance is considered somewhat dull.

*Leaf pubescence.*—Generally present on the ventral surface only, and covering about 100% of the surface area.

*Surface texture, leaf pubescence.*—Fine.

*Leaf pubescence.*—Color — White (RHS 155B).

*Leaf blade length.*—About 77.6 mm to about 90.4 mm.

*Leaf blade width.*—About 54.8 mm to about 72.6 mm.

*Marginal form.*—Shape — Generally considered bi-serrate. Occasionally a few tri-serrate regions may be found.
*Leaf tip.*—Shape — Acuminate.
*Leaf base.*—Shape — Rounded.
*Leaf stipules.*—Numbers — 2 per petiole are typically found.
*Leaf stipules.*—Length — About 8.6 mm to about 14.1 mm.
*Leaf stipules.*—Width — About 1.5 mm to about 3.1 mm.
*Leaf stipules.*—Color — The dorsal surface is yellow-green (RHS 147B). The ventral surface has a lighter yellow-green color (RHS 144B).
*Leaf stipules.*—Pubescence — Present on both the dorsal and ventral surfaces thereof.
*Pubescence.*—Surface Texture — Considered fine. The leaf pubescence covers 10% of the dorsal surface, and about 50% of the ventral surface. The leaf pubescence color is white (RHS Group 155B).
*Leaf blade color.*—Dorsal Surface — Yellow/green (RHS 147A).
*Leaf blade color.*—Ventral Surface — Yellow/green (RHS 148B).
*Leaf mid-vein.*—Shape — Prominent and having a fine pubescence on the ventral surface thereof.
*Leaf mid-vein.*—Width — About 1.4 mm when measured at mid-blade.
*Leaf mid-vein.*—Color — The dorsal surface has a color of yellow (RHS 150D).
*Mid-vein.*—Pubescence — The color of the pubescence is white (RHS 155B).
*Petiole.*—Length — About 18.3 to 26.8 mm.
*Petiole.*—Diameter — About 1.6 mm to about 2.4 mm.
*Petiole.*—Color — Yellow/green (RHS 149D).
*Petiole.*—Pubescence — Generally considered abundant, and fine in texture, and which further extends over the entire length and circumference of the petiole.
*Pubescence color.*—White (RHS 155B).

FLOWERS

*Date of full bloom.*—In 2010, this occurred on April 23.
*Number of blooms per bud.*—Typically 5 to 6 appear, mostly 6.
*Flower size.*—Generally — Considered medium to medium large.
*Diameter when fully expanded.*—About 44 mm to about 47.4 mm.
*Flower petals.*—Width — About 15.7 mm.
*Flower petals.*—Length — About 22.4 mm.
*Leaf petals.*—Color — White and having gray/purple highlights (RHS N66D).
*Petal vein color.*—Red/purple (RHS 67A).
*Flower stamens.*—Numbers — Variable from 19 to 21 may be found.
*Flower filaments.*—Length — About 3.1 mm to 7.8 mm.
*Flower stamens.*—Color — Gray/yellow (RHS 160D).
*Flower anthers.*—Shape — Kidney-like, and having a width of about 1.5 mm, and a length of about 1.8 mm.
*Flower anthers.*—Color: Mature anthers have a yellow-like color (RHS 158B).
*Flower pistil.*—Length — About 11.8 to 12.7 mm.
*Styles.*—Numbers — 5. The styles are typically fused near the base, and have a white pubescence which appears at the union.
*Styles.*—Length — About 9.5 mm.
*Styles.*—Color — Yellow/green (RHS 149D).
*Stigma.*—Shape — Club-like.
*Stigma.*—Color — Gray/yellow (RHS 162A).
*Sepals.*—Numbers — 5 per blossom.
*Sepals.*—Shape — Curled back towards the peduncle. The overall shape is considered deltoid with the tip having an acuminate shape, and the base being truncate in appearance.
*Sepals.*—Length — About 7.4 mm.
*Sepals.*—Width — About 4 mm.
*Sepals.*—Surface Texture — Having pubescence on both the dorsal and ventral surfaces.
*Sepal color.*—Green (RHS 143C), however the sepal tips, are highlighted with a gray/purple color (RHS 186A).
*Peduncle.*—Length — About 15.4 to about 23.8 mm.
*Peduncle.*—Color — Green (RHS 138B).
*Peduncle.*—Surface Texture — Considerable white downiness is present over the entire surface.

FRUIT

*Maturity when described.*—Generally the fruit produced by the present variety of apple tree is described hereinafter as it would be found at full commercial maturity. In this regard the fruit of the present variety was ripe for commercial harvesting and shipment under the ecological conditions prevailing near Ephrata, Wash. on Sep. 4, 2010. In relative comparison to the 'Honeycrisp' apple tree which is grown at the same geographical location, and under the same cultural conditions, the fruit produced by the 'Honeycrisp' apple tree was ripe for harvesting and shipments 5 days later.
*Fruit form.*—Considered generally short, oblate and having symmetrical sides. The fruit further has an equatorial diameter which is regular.
*Fruit size.*—Considered large for the species at normal crop loads.
*Average equatorial diameter.*—About 90.1 mm.
*Average axial diameter.*—About 75.6 mm.
*Stem.*—Length — Considered stout and having a length of about 23.3 mm.
*Stem.*—Diameter — About 3.3 mm.
*Stem cavity.*—Average Width — About 41 mm.
*Stem cavity.*—Average Depth — About 21.1 mm.
*Stem cavity.*—Shape — Obtuse.
*Stem cavity.*—Lipping — None appears evident.
*Basin cavity.*—Width — About 32.9 mm.
*Basin cavity.*—Shape — Considered abrupt.
*Eye.*—Shape — Considered Abrupt.
*Eye.*—Shape — Considered erect, and having a connivent tip.
*Eye.*—Sepal color — Green (RHS 138B).
*Sepal surface texture.*—Downy and white colored (RHS 155D).
*Fruit skin.*—Surface texture — Glabrous and having a moderate bloom.
*Skin appearance.*—Having a blotchy striped pattern. This striped pattern is more intense in color on the side of the fruit having more light exposure.

*Skin color.*—Generally — The striping appearing on the fruit is red (RHS 46A).

*Skin undercolor.*—Yellow/green (RHS 150C).

*Fruit lenticels.*—Generally — Present, yet small and somewhat indistinct. They are more numerous when viewed from the Calyx end.

*Lenticels.*—Numbers — about 5 are found per square cm of surface area at the calyx.

*Lenticels.*—Shape — Round and having a size of about 0.3 to about 0.6 mm diameter. Lenticel Color — White (RHS Group 155D).

*Fruit core.*—Position — Considered median.

*Core line position.*—Considered median clasping.

*Core length.*—About 31.7 mm.

*Core diameter.*—About 29.4 mm.

*Core shape.*—Generally — Considered flat and conical.

*Cell.*—Numbers — Typically 5 per fruit are found.

*Cell generally.*—Considered tufted and having narrow lines circumventing the cell walls. The tuft color is white (RHS 155C).

*Cell shape.*—Obovate.

*Cell shape.*—Length — About 21 mm.

*Cell shape.*—Width — About 12.4 mm.

*Cell shape.*—Depth — About 9.5 mm.

*Tube.*—Shape — Cone shaped.

*Stamen position.*—Considered basal.

*Axis.*—Orientation — Considered axial and closed.

*Seed number.*—2.

*Seed shape.*—Considered acute.

*Seed length.*—About 9.6 to 10.4 mm.

*Seed width.*—About 5.4 to about 5.8 mm.

*Seed color.*—Gray/orange (RHS 165A).

*Fruit flesh.*—Generally — Considered firm, crisp, melting and juicy.

*Flesh color.*—Yellow/white (RHS 158D).

*Flesh aroma.*—Apple-like and mild in intensity.

*Harvesting date.*—Sep. 4, 2010. In comparison, the 'Honeycrisp' apple tree (U.S. Plant Pat. No. 7,197), ripened at the same geographical location, on Sep. 9, 2010.

*Fruit pressure.*—Generally — 12.8 lbs. This is less than the fruit pressure expressed by the fruit of the 'Honeycrisp' apple tree which is 13.8 pounds.

*Brix.*—The present variety has a brix of 13.1. In comparison, the fruit produced by the 'Honeycrisp' apple tree has fruit having a brix of 13.8.

*pH.*—The present variety has a pH of about 3.35. This is similar to the pH measured in the fruit of the 'Honeycrisp' apple tree (U.S. Plant Pat. No. 7,197).

*Fruit keeping quality.*—Considered very good. The fruit of the present variety has been kept up to four months in cold storage with no deleterious effects noted.

*Fruit browning.*—The present variety resists browning after being exposed to ambient air.

*Pollination.*—Any diploid apple that blooms in the same season may be utilized with the present variety of apple tree.

*Fruit use.*—Considered to be a fresh desert apple.

*Disease and insects resistance.*—The present variety is considered to be susceptible to all insects and diseases found in the central Washington State region.

Although the new variety of apple tree possesses the described characteristics when grown under the ecological conditions prevailing in Ephrata, Wash., in the south-central part of Washington State, it should be understood that variations of the usual magnitude, and characteristics incident to changes in growing conditions, fertilization, pruning and pest control, as well as horticultural management practice are to be expected.

Having thus described and illustrated my new variety of apple tree, what I claim is new, is a desire to secure by Plant Letters Patent is:

1. A new and distinct variety of apple tree, *Malus domestica* substantially as illustrated and described, and which is characterized principally as to novelty by bearing an attractively colored apple which is ripe for harvesting and shipment about September $4^{th}$ under the ecological conditions prevailing near Ephrata, Wash.

* * * * *